US012168119B1

(12) United States Patent
Simpson, IV et al.

(10) Patent No.: US 12,168,119 B1
(45) Date of Patent: Dec. 17, 2024

(54) PERITONSILLAR ABSCESS ASPIRATION KIT AND METHOD OF USE

(71) Applicant: 9 Line Development Group, Inc., Tampa, FL (US)

(72) Inventors: William Cyril Simpson, IV, Tampa, FL (US); Meagan Mackey Bentinck, Dana Point, CA (US)

(73) Assignee: 9 Line Development Group, Inc., Tampa, FL (US)

( * ) Notice: Subject to any disclaimer, the term of this patent is extended or adjusted under 35 U.S.C. 154(b) by 0 days.

(21) Appl. No.: 18/489,322

(22) Filed: Oct. 18, 2023

Related U.S. Application Data

(60) Provisional application No. 63/421,297, filed on Nov. 1, 2022.

(51) Int. Cl.
  *A61M 5/32* (2006.01)
  *A61B 17/34* (2006.01)
  *A61M 19/00* (2006.01)

(52) U.S. Cl.
  CPC .......... *A61M 5/3286* (2013.01); *A61B 17/34* (2013.01); *A61M 19/00* (2013.01)

(58) Field of Classification Search
  CPC ...... A61M 5/32; A61M 5/3205; A61M 5/321; A61M 5/3202; A61M 2005/3212; A61M 5/3213; A61M 2005/328; A61M 5/34; A61M 5/3286; A61M 19/00; A61B 17/34
  See application file for complete search history.

(56) References Cited

U.S. PATENT DOCUMENTS

| | | | | |
|---|---|---|---|---|
| 5,180,371 | A * | 1/1993 | Spinello | A61M 5/2053 604/512 |
| 2002/0108614 | A1 * | 8/2002 | Schultz | A61M 16/0486 128/207.14 |
| 2014/0296868 | A1 * | 10/2014 | Garrison | A61B 17/22 606/127 |
| 2016/0206834 | A1 * | 7/2016 | Shluzas | A61M 5/508 |

* cited by examiner

*Primary Examiner* — Jason E Flick
(74) *Attorney, Agent, or Firm* — Nicholas Pfeifer; Smith & Hopen, P. A.

(57) ABSTRACT

A peritonsillar abscess aspiration kit. The kit includes at least one aspiration needle and one anesthetic application needle. Each needle has a corresponding needle guard and guard cap configured to house the needle. In addition, each needle has a length greater than the needle guard. The kit further includes at least one syringe configured to attach to the needles and a syringe actuator. The syringe actuator is configured to securely house the syringe and includes a pistol grip and a trigger configured to translate a plunger in the syringe when the trigger is pulled.

19 Claims, 13 Drawing Sheets

PERITONSILLAR ABSCESS ASPIRATION KIT AND METHOD OF USE

CROSS-REFERENCE TO RELATED APPLICATIONS

This nonprovisional application claims priority to provisional application No. 63/421,297, entitled "PERITONSILLAR ABSCESS ASPIRATION KIT AND METHOD OF USE," filed Nov. 1, 2022 by the same inventors.

BACKGROUND OF THE INVENTION

1. Field of the Invention

This invention relates, generally, to medical device kits and medical procedures. More specifically, it relates to peritonsillar abscess aspiration procedures and medical device kits for performing the same.

2. Brief Description of the Prior Art

Peritonsillar abscesses are the most common deep infection of the head/neck region in young adults. Peritonsillar abscesses result from a severe case of tonsillitis in which the infection spreads behind one or more tonsils. While antibiotics can treat an early infection, sometimes the abscess needs to be drained of pus. This procedure is called peritonsillar abscess aspiration.

In order to aspirate the abscess, a trained clinician first applies an anesthetic to the abscess and surrounding area. This step typically includes a 5-mL syringe and a 25-gauge needle. The clinician inserts the needle into a vial to extract the anesthetic and then depresses the patient's tongue to apply the anesthetic around the abscess.

Once the anesthetic has taken effect, the clinician can use a syringe and needle to aspirate the abscess. Typically, the syringe is a 10-mL syringe and the needle is an 18-20 gauge needle. A first clinician uses the tongue depressor and a suction tube, while a second clinician free hands the aspiration syringe and needle. However, clinicians must limit the depth of the aspiration needle to avoid unintentionally hitting critical tissue behind the abscess. Unfortunately, judging the depth of the aspiration needle can be difficult.

Accordingly, what is needed is a standardized peritonsillar aspiration kit that provides clinicians with all the tools necessary to aspirate the abscess and ensures that the components are securely configured to operate together without the risk of human error and failure. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a standardized peritonsillar aspiration kit that provides clinicians with all the tools necessary to aspirate the abscess and ensures that the components are securely configured to operate together without the risk of human error and failure is now met by a new, useful, and nonobvious invention.

The present invention includes a peritonsillar abscess aspiration kit. The kit comprises a hollow aspiration needle having a length extending between a distal tip and a proximal needle hub. In addition, the distal tip is tapered to a point sufficient to puncture an abscess. The kit further includes an aspiration needle guard. The aspiration needle guard has an internal lumen sufficiently sized to receive the aspiration needle therein. Moreover, the aspiration needle guard has a length extending between a first end and a second end wherein the length of the needle guard is less than the length of the aspiration needle. As a result, a distal section of the aspiration needle extends beyond the second end of the needle guard when the aspiration needle resides within the internal lumen of the needle guard. In some embodiments, the aspiration needle extends about 1 to 1.5 centimeters beyond the distal end of the aspiration needle guard when secured within the internal lumen of the aspiration needle guard.

The kit also includes an aspiration needle guard cap. The aspiration needle guard cap has a closed distal end and an open proximal end leading to an internal cavity. The internal cavity is sufficiently sized to receive the distal section of the aspiration needle that extends beyond the second end of the aspiration needle guard when the aspiration needle resides within the internal lumen of the aspiration needle guard. The aspiration needle guard cap and aspiration needle guard are configured to temporarily attach to each other to enclose the aspiration needle when not in use. In some embodiments, the aspiration needle, aspiration needle guard, and the aspiration needle guard cap are pre-assembled with the aspiration needle residing within the internal lumen of the aspiration needle guard and the internal cavity of the aspiration needle guard.

The kit additionally includes an anesthetic application needle, an anesthetic needle guard, and anesthetic needle guard cap. The anesthetic application needle has a length extending between a distal tip and a proximal needle hub that is greater than a length extending between a first end and a second end of the anesthetic needle guard. In addition, the anesthetic application needle is sized to fit within an internal lumen in the anesthetic needle guard. As a result of the length difference, a distal section of the anesthetic application needle extends beyond the second end of the anesthetic needle guard when the anesthetic application needle resides within the internal lumen of the anesthetic needle guard.

The anesthetic needle guard cap includes a closed distal end and an open proximal end leading to an internal cavity. The internal cavity is sufficiently sized to receive the distal section of the anesthetic application needle that extends beyond the second end of the anesthetic needle guard when the anesthetic application needle resides within the internal lumen of the anesthetic needle guard. In some embodiments, the anesthetic application needle, anesthetic needle guard, and the anesthetic needle guard cap come pre-assembled with the anesthetic application needle residing within the internal lumen of the anesthetic needle guard and the internal cavity of the anesthetic needle guard cap.

At least one syringe and a syringe actuator can also be included in the kit. The syringe is configured to attach to the aspiration needle and the anesthetic application needle. The syringe actuator is configured to securely house the syringe and has pistol grip and a trigger configured to proximally translate a plunger in the syringe when the trigger is pulled.

In some embodiments, such as those described above, the kit further includes a vial of anesthetic, an anesthetic retrieval needle for retrieving anesthetic from the vial, a suction tube, multiple syringes, and/or a tongue depressor with a light source.

The invention also includes a peritonsillar abscess aspiration needle assembly. The assembly includes an aspiration needle, an aspiration needle guard, and an aspiration needle guard cap pre-assembled with the aspiration needle residing within the internal lumen of the aspiration needle guard and the internal cavity of the aspiration needle guard. The aspiration needle is a hollow needle with a length extending between a distal tip and a proximal needle hub. The distal tip is tapered to a point sufficient to puncture an abscess.

The aspiration needle guard has an internal lumen sufficiently sized to receive the aspiration needle therein. Moreover, the aspiration needle guard has a length extending between a first end and a second end wherein the length of the needle guard is less than the length of the aspiration needle. As a result, a distal section of the aspiration needle extends beyond the second end of the needle guard when the aspiration needle resides within the internal lumen of the needle guard.

The aspiration needle guard cap has a closed distal end and an open proximal end leading to an internal cavity. The internal cavity is sufficiently sized to receive the distal section of the aspiration needle that extends beyond the second end of the aspiration needle guard when the aspiration needle resides within the internal lumen of the aspiration needle guard. The aspiration needle guard cap and aspiration needle guard are configured to temporarily attach to each other to enclose the aspiration needle when not in use. In some embodiments, the aspiration needle guard and/or the aspiration needle guard cap are transparent.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, the term "about" means approximately or nearly, and in the context of a numerical value or range, the term means±15% of the numerical value.

The present invention includes a peritonsillar abscess aspiration kit (the "kit") 102 that includes a plurality of predesigned components configured to improve the efficiency, safety, and efficacy of performing peritonsillar abscess aspiration procedures. Some embodiments of the present invention include a method of using kit 102 and its components to aspirate a peritonsillar abscess.

Figure 1:
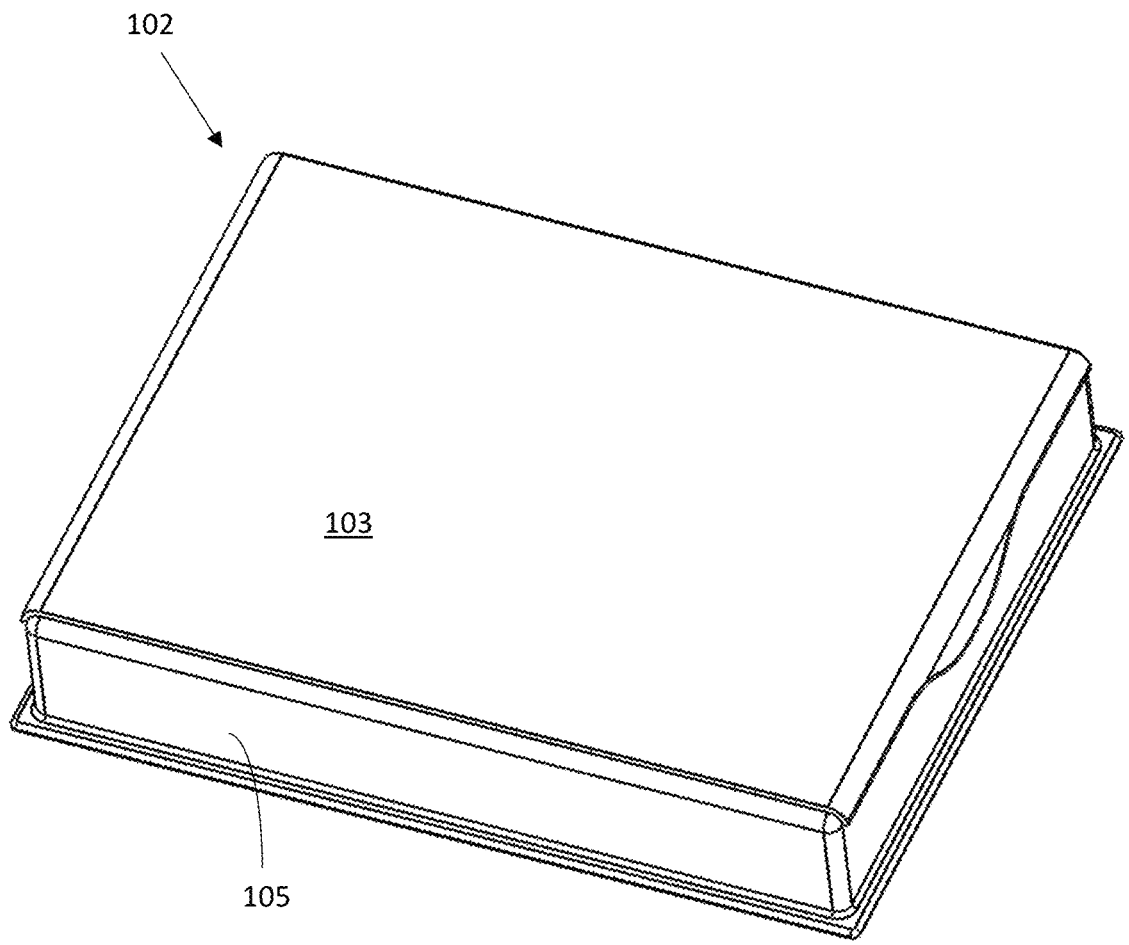
FIG. 1 is a perspective view of a peritonsillar abscess aspiration kit.
Figure 2:
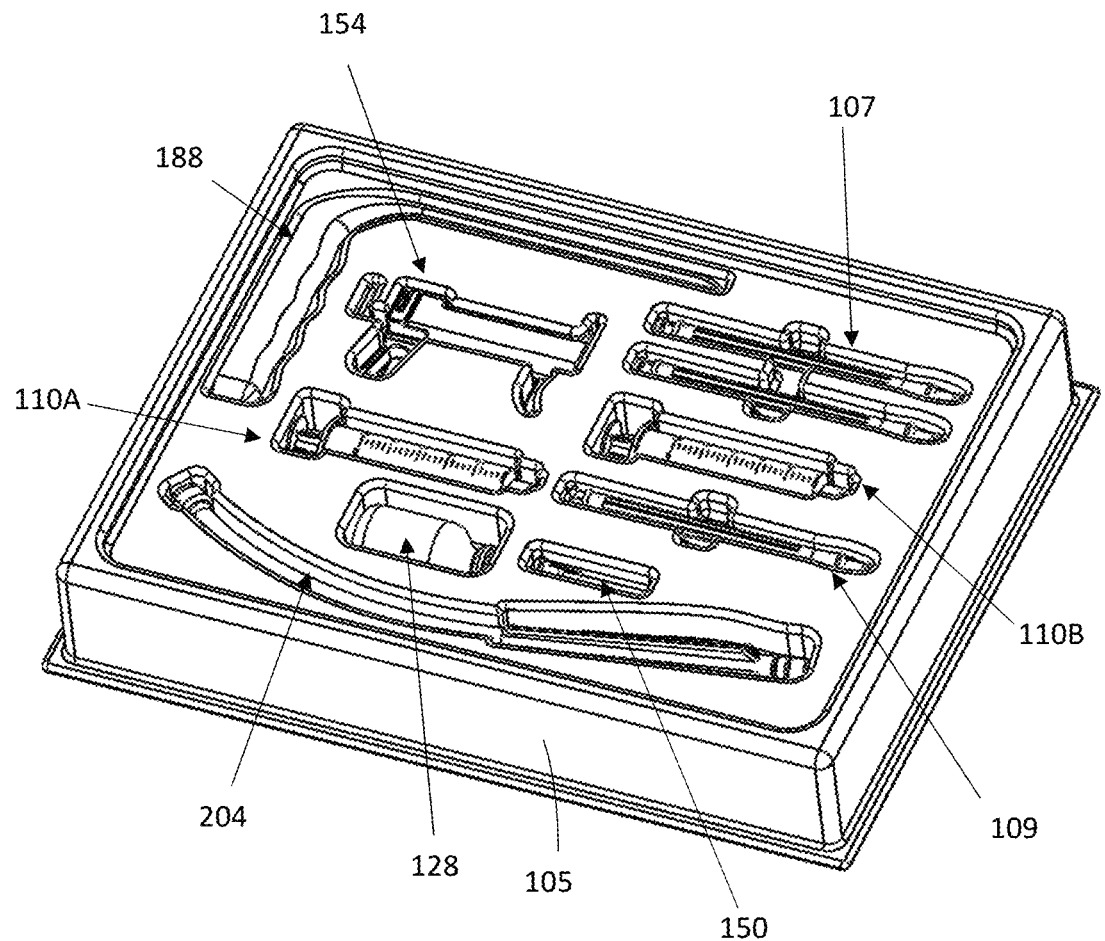
FIG. 2 is a perspective view of a peritonsillar abscess aspiration kit with the lid removed.
Figure 3:
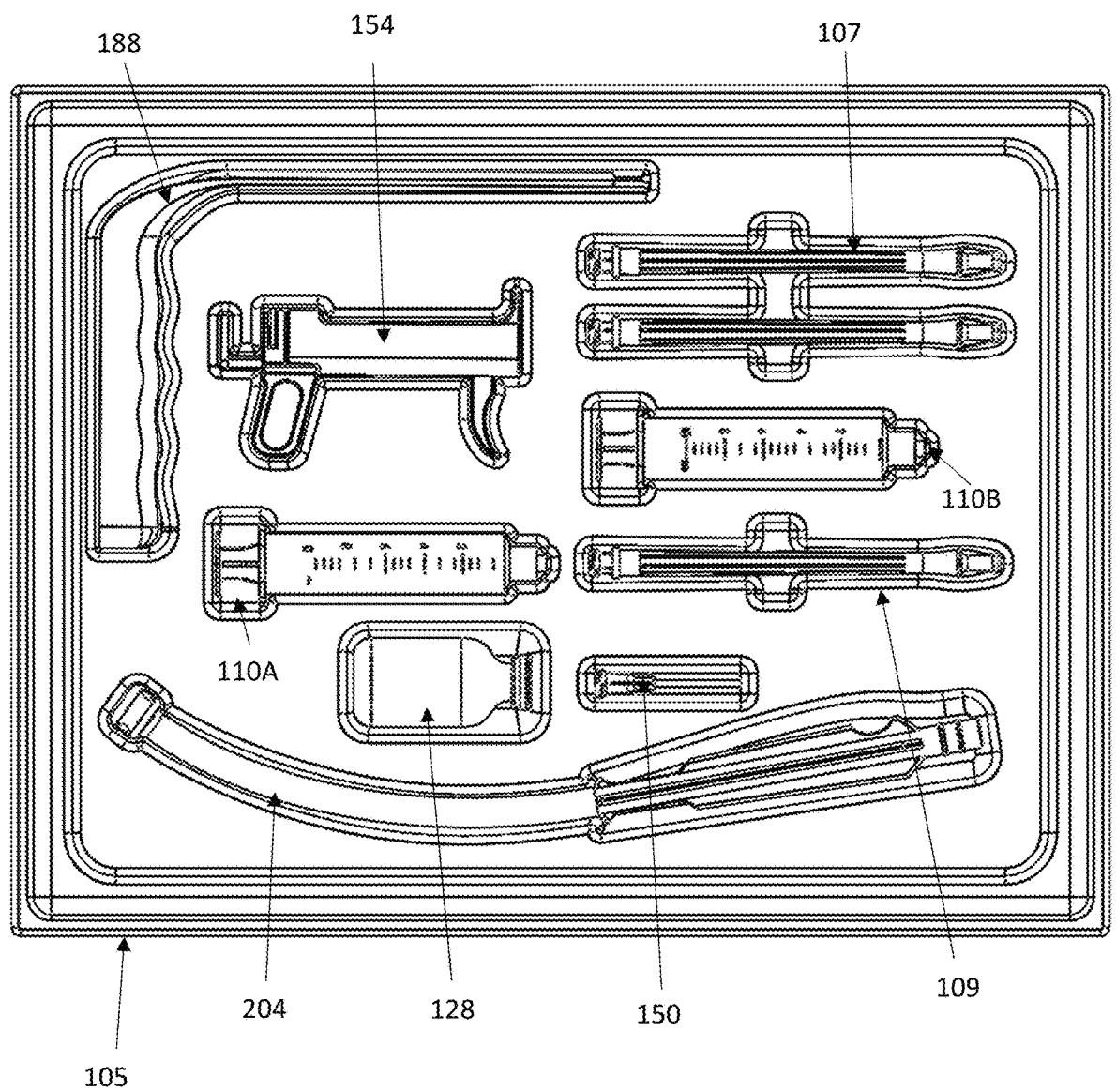
FIG. 3 is a plan view of the kit from FIG. 2.

As provided in FIGS. 1-3, kit 102 includes a housing 103 and lid 105. Housing 103 is configured to retain the various components of kit 102. While kit 102 depicts a series of recesses 107 with each configured to receive a component, kit 102 may retain the components through other known approaches.

Figure 4:
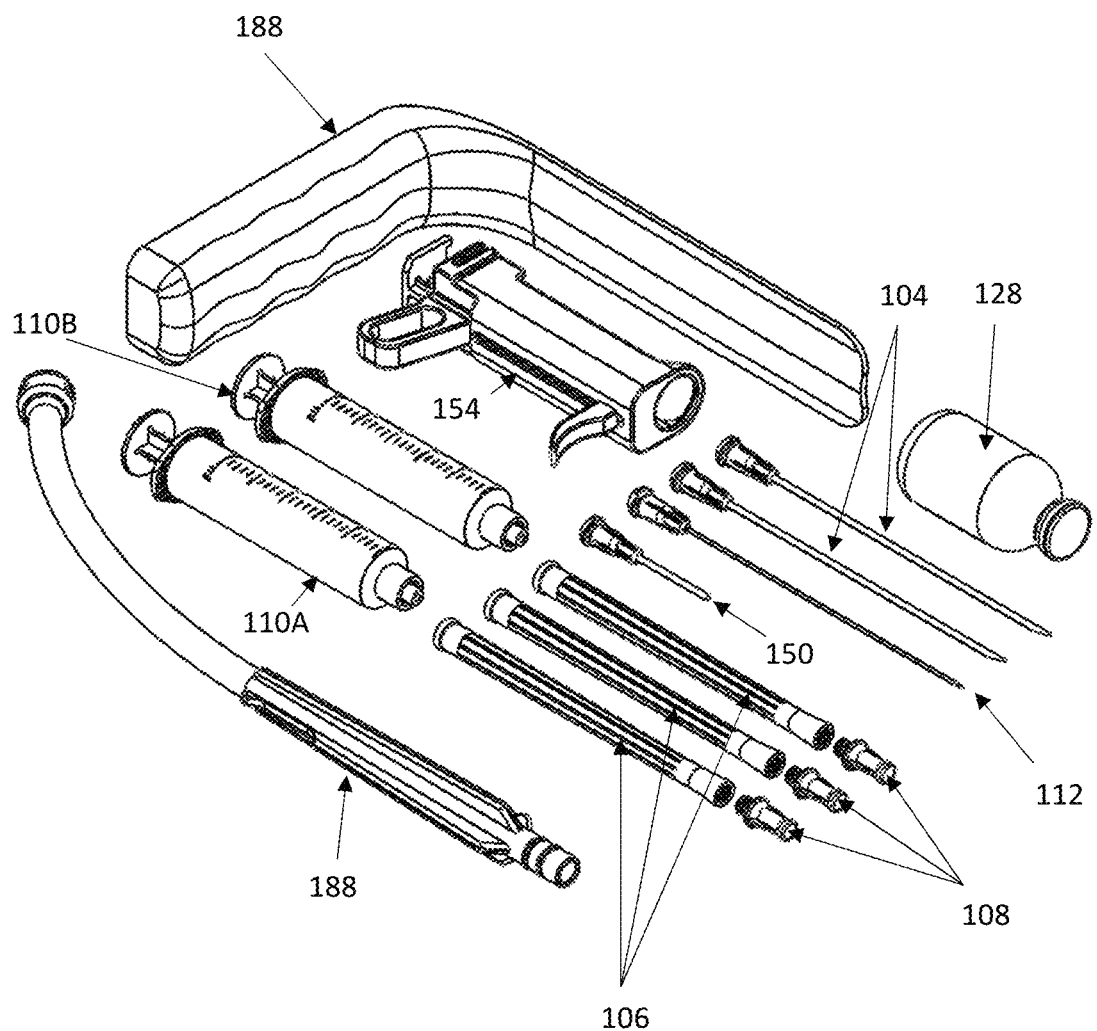
FIG. 4 is a perspective view of the components of the kit removed from the kit housing.

As shown best in FIGS. 2-4, an embodiment of kit 102 includes one or more needle assemblies (e.g., aspiration needle assemblies 107 and anesthetic application needle assemblies 109) with each assembly 107, 109 including a corresponding needle 104, 112, needle guard 106, and guard cap 108. Kit 102 further includes at least one syringe 110 configured to securely connect to at least the provided needles 104, 112. In some embodiments, kit 102 includes at least one anesthetic application needle 112, which can be provided as needle assembly 109, and at least one aspiration needle 104, which can be provided as needle assembly 107. In some embodiments, kit 102 includes two aspiration needles 104, which can be provided as needle assemblies 107.

Anesthetic application needle 112 has an internal lumen to deliver anesthetic 113 to the abscess and the localized area around the abscess. To ensure that anesthetic 113 is applied accurately, anesthetic application needle 112 has a length of roughly 10 centimeters. A length of 10 centimeters ensures that distal end 114 of anesthetic application needle 112 will reach the back of the patient's mouth where the peritonsillar abscess is typically located. In some embodiments, the length of anesthetic application needle 112 is between 3.5 and 4 inches. In some embodiments, the length of anesthetic application needle 112 is greater than or equal to 3.5 inches.

Figure 5:
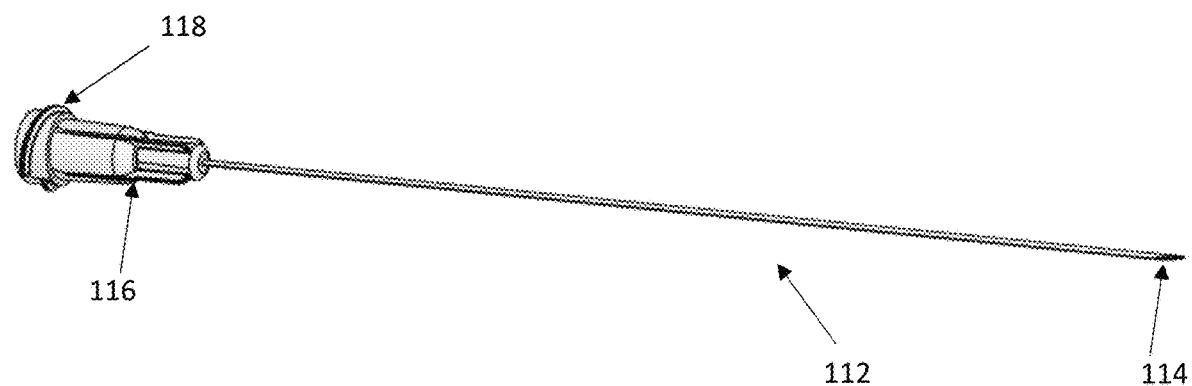
FIG. 5 is a perspective view of an embodiment of the anesthetic application needle.

Anesthetic application needle 112, as isolated in FIG. 5, is a 25-gauge needle, which is a preferred size for delivering local anesthetics. However, anesthetic application needle 112 can have an internal diameter of a different size sufficient to deliver local anesthetics through its internal lumen and into the tissue of the patient.

Distal end 114 of anesthetic application needle 112 has a sharp point to allow anesthetic application needle 112 to puncture the patient's tissue. However, some embodiments of anesthetic application needle 112 may have a blunt distal end if the anesthetic is a topical agent.

Figure 6:
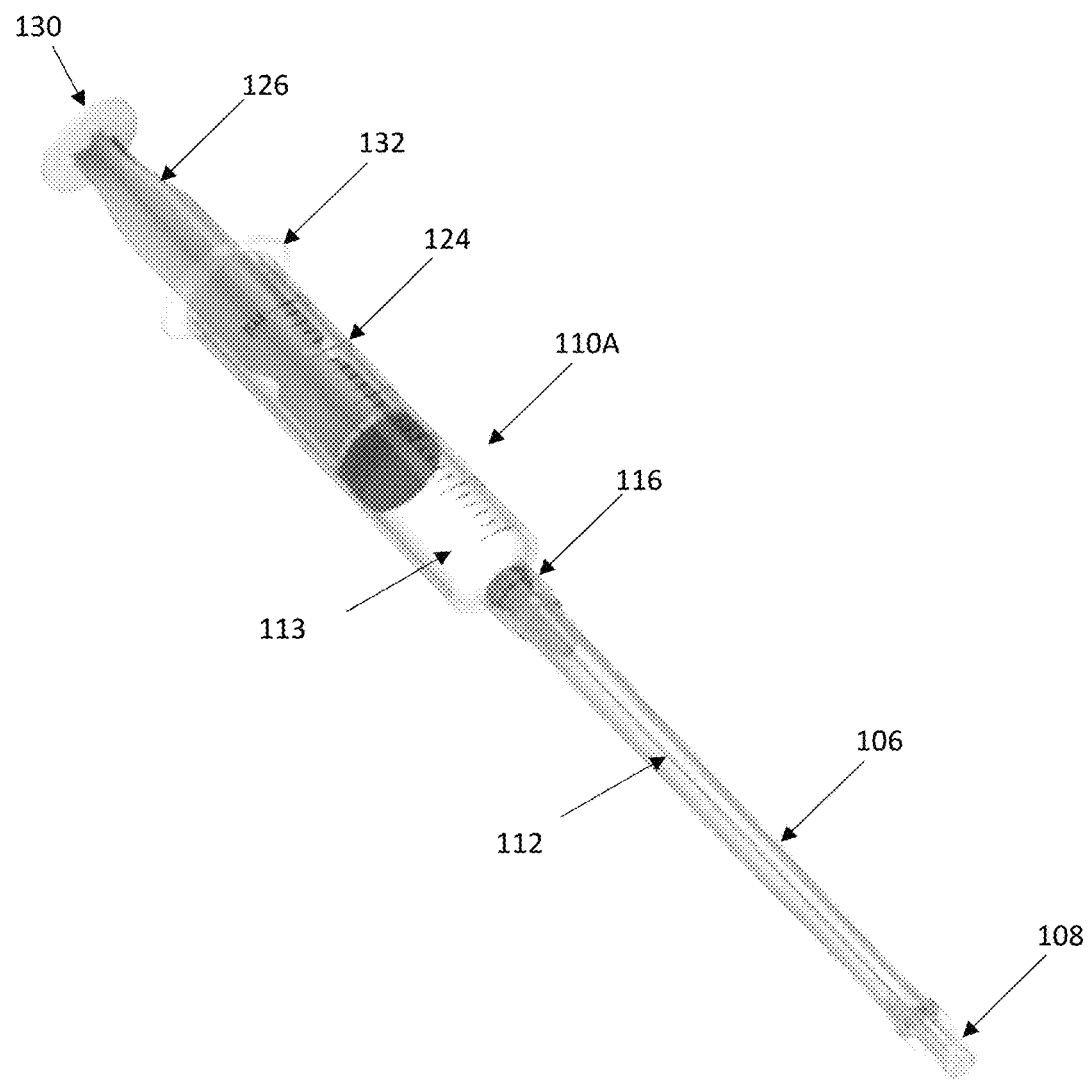
FIG. 6 is an assembly view of a syringe, the anesthetic application needle, needle guard, and guard cap.

The proximal end of anesthetic application needle 112 is configured to securely engage distal end 111 of syringe 110 as shown in FIG. 6. Some configurations include needle hub 116 with adapter 118 configured to engage distal end 111 of syringe 110. In some embodiments, needle adapter 118 is configured to temporarily attach to syringe 110. Adapter 118 can be those common in the medical device industry, such as a luer lock. For example, adapter 118 of anesthetic application needle 112 can be comprised of a male luer fitting as depicted in FIG. 5 and distal end 111 of syringe 110 can include a corresponding female luer fitting, or vice versa.

Figure 7:
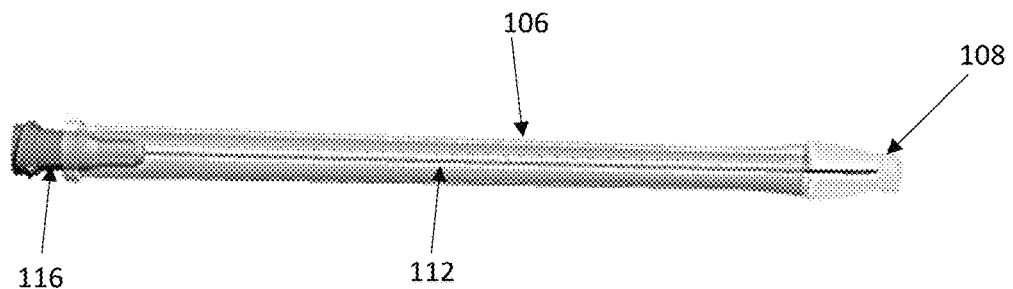
FIG. 7 is an assembly view of the anesthetic application needle, needle guard, and guard cap.

Needle hub 116 is also configured to temporarily engage needle guard 106 as shown in FIG. 7. Needle guard 106 will be covered in subsequent sections. Needle hub 116 can be any design configured to temporarily engage the proximal end of needle guard 106. In some embodiments, needle hub 116 is a tapered shape moving in a distal direction to allow proximal end 122 of needle guard 106 to be press fit onto needle hub 116. In some embodiments, needle hub 116 includes one or more interacting elements to operably engage needle guard 106 and temporarily secure needle guard 106 to needle 104, 112.

Kit 102 also includes at least one aspiration needle 104. Some embodiments include multiple aspiration needles 104 to allow clinicians to more efficiently and safely extract multiple syringes worth of pus from the abscess. For example, some embodiments include at least two aspiration needles 104 and two syringes 110.

Figure 8:
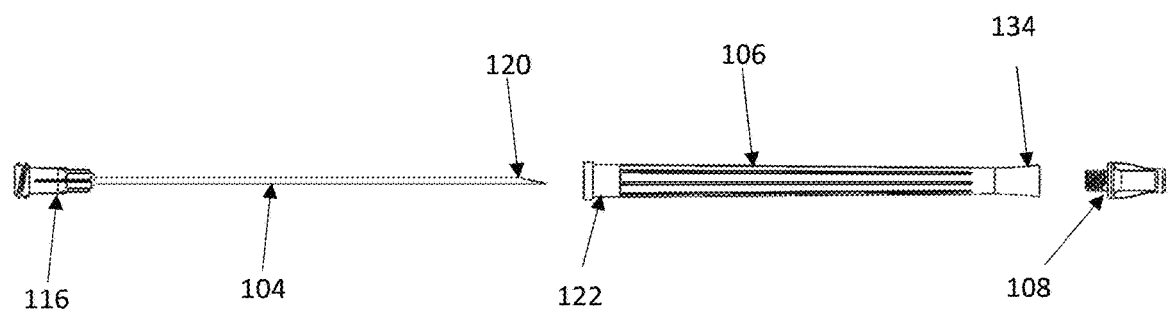
FIG. 8 is an exploded view of an assembly of an aspiration needle, needle guard, and guard cap.

Referring now to FIG. 8, each aspiration needle 104 has an internal lumen to provide a channel for extracting pus from the abscess. To ensure that aspiration needle 104 reaches the peritonsillar abscess, aspiration needle 104 has a length of roughly 10 centimeters. A length of 10 centimeters ensures that distal end 120 of aspiration needle 104 can puncture the peritonsillar abscess in the back of the mouth. In some embodiments, the length of aspiration needle 104 is between 3.5 and 4 inches. In some embodiments, the length of aspiration needle 104 is greater than or equal to 3.5 inches.

Aspiration needle 104 is an 18-gauge needle, which is a preferred size for extracting pus from an abscess. However, aspiration needle 104 can have an internal diameter of a different size sufficient to extract pus from an abscess. In addition, distal end 120 of aspiration needle 104 has a sharp point to allow aspiration needle 104 to puncture the peritonsillar abscess.

Figure 9:
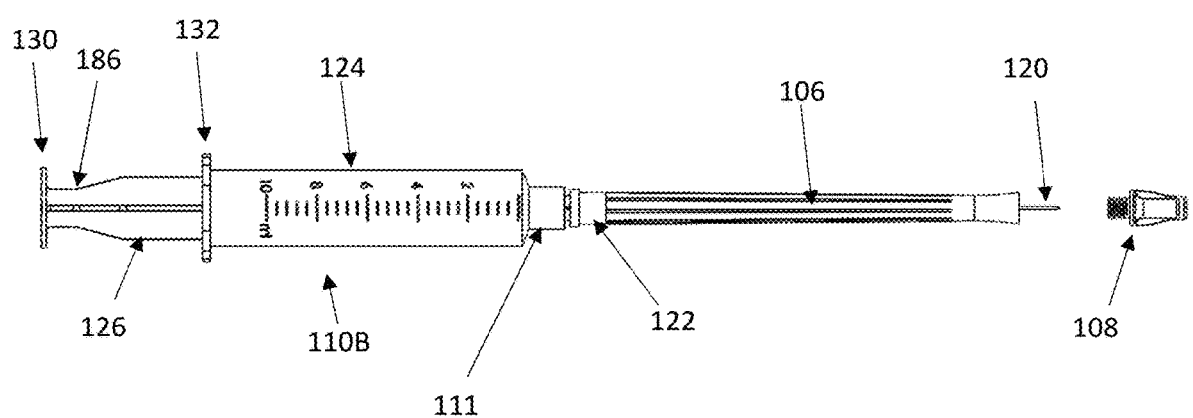
FIG. 9 is an assembly view of a syringe, the aspiration needle, and needle guard with the guard cap separated from the needle guard.

Like anesthetic application needle 112, the proximal end of aspiration needle 104 is configured to securely engage distal end 111 of one of syringes 110 as exemplified in FIG. 9. Some configurations also include needle hub 116 with adapter 118 configured to engage distal end 111 of syringe 110. In some embodiments, needle adapter 118 is configured to temporarily attach to syringe 110. Needle adapter 118 can be those common in the medical device industry, such as a luer lock. For example, needle adapter 118 of aspiration needle 104 can include a male luer fitting and distal end 111 of syringe 110 can include a corresponding female luer fitting, or vice versa.

As previously noted, kit 102 further includes at least one syringe 110. In some embodiments, kit 102 includes multiple syringes 110. Kit 102 may include one syringe for the retrieval and application of the anesthetic ("anesthetic syringe 110A") and one or more syringes for aspirating the abscess ("aspiration syringes 110B"). Anesthetic syringe 110A may be smaller in size or have a smaller internal volume due to the limited amount of anesthetic fluid typically used for the procedure. For example, anesthetic syringe 110A may have a volume less than or equal to 10 milliliters. In some embodiments, anesthetic syringe 110A has a volume of 5 milliliters. In contrast, each aspiration syringe 110B can have a larger volume due to the potential large volume of the peritonsillar abscess. In some embodiments, each aspiration syringe 110B has a volume equal to or greater than 10 mL.

Each syringe 110 comprises barrel 124 and plunger 126 slidably disposed therein. Plunger 126 is configured to be pulled proximally from barrel 124 to extract material, such as pus from the abscess or anesthetic 113 from vial 128. In some embodiments, plunger 126 includes at least one plunger flange 130 located near the proximal end of plunger 126. Flange 130 extends in a generally lateral direction relative to the length/longitudinal axis of plunger 126. In some embodiments, the proximal end of plunger 126 includes at least two flanges 130 or includes an annular flange 130 extending about the circumference of the proximal end of plunger 126.

Barrel 124 may also have at least one flange 132 located near the proximal end of barrel 124. Barrel flange 132 also extends in a generally lateral direction relative to the length/longitudinal axis of barrel 124. In some embodiments, the proximal end of barrel 124 includes at least two flanges or includes an annular flange 132 extending about the circumference of the proximal end of barrel 124.

Distal end 111 of each syringe 110 is configured to operably attach to needles 104, 112 in kit 102. Syringes 110 and needles 104, 110 are configured to temporarily connect to each other. In some embodiments, distal end 111 of each syringe 110 includes a female luer fitting configured to receive the male luer fitting of one of needles 104, 112. In some embodiments, each needle 104, 112 and each syringe 110 includes the same attachment components to allow for versatility. However, some embodiments include anesthetic application needle(s) 112 and anesthetic syringe(s) 110A having distinct attachment components relative to aspiration needle(s) 104 and aspiration syringe(s) 110B, thereby ensuring that aspiration needle(s) 104 will only connect with the aspiration syringe(s) 110B and that anesthetic application needle(s) 112 will only connect to the anesthetic syringe(s) 110A.

In some embodiments, each aspiration needle 104 includes a corresponding aspiration syringe 110B preconnected to needle 104 in an operable configuration such as the configuration shown in FIG. 6. In some embodiments, aspiration needle(s) 104 are permanently attached to their corresponding syringe(s) 110B. The preconnected or permanent attachments reduce prep time and complexity while increasing safety.

Kit 102 further includes one or more needle guards 106. In some embodiments, kit 102 includes an equal number of guards 106 as aspiration needles 104 and/or an equal number of guards 106 as anesthetic application needles 112. In some embodiments, as shown in FIGS. 2-3, each of aspiration and anesthetic application needles 104, 112 is pre-packaged within its respective needle guard 106 to improve safety.

As best shown in FIGS. 7-9, each needle guard 106 includes a main body extending between proximal end 122 and distal end 134. The main body includes an internal lumen sized to receive one of needles 104, 112. Proximal end 122 includes an opening to the internal lumen that is configured to connect to needle hub 116. In some embodiments, needle guard 106 is locked or permanently secured to needle hub 116. The locking or attachment mechanism can be any known in the art, including but not limited to single piece construction, adhesives, welding, etc. In some embodiments, needle guard 106 is temporarily secured to needle hub 116. The temporary attachment may be achieved through known approaches including but not limited to press fitting, cam locks, resilient clips, detents, threading, luer locks, etc.

Figure 15:
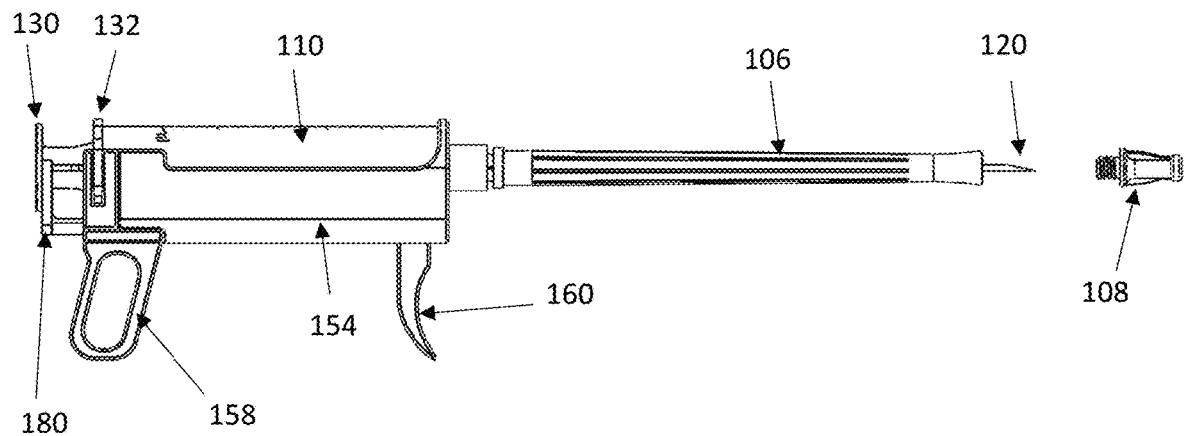
FIG. 15 is a side view of the assembly in FIG. 14 with the guard cap removed.
Figure 16:
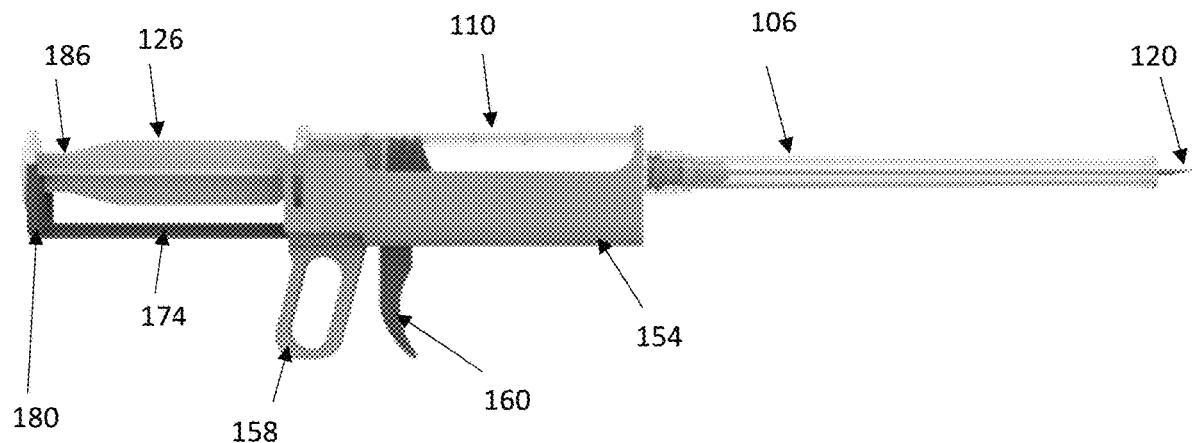
FIG. 16 is a side view of the assembly in FIG. 15 with the trigger pulled and the plunger in the extracted position.

The main body of each needle guard 106 has a specific length relative to the needle it guards. Embodiments of both aspiration needle(s) 104 and anesthetic application needle(s) 112 are intended to puncture the patient's tissue, but needle guards 106 are intended to remain in place when needles 104, 112 are in use. Thus, distal ends 120 of needles 104, 112 need to extend beyond needle guards 106 to puncture the patient's tissue. To do so, needle guards 106 have a length that is less than the length of needles 104, 112 for which needle guard 106 is intended to guard as shown in FIGS. 9 and 15-16. In some embodiments, each needle guard 106 has a length that is 1 centimeter less than the length of needle 104, 112. In some embodiments, each needle guard 106 has a length that allows for roughly 1 centimeter of needle 104, 112 to extend distally beyond distal end 134 of needle guard 106. In some embodiments, each needle guard 106 has a length that allows for between 1 and 1.5 centimeters of needle 104, 112 to extend distally beyond distal end 134 of needle guard 106. In some embodiments, each needle guard 106 has a length that allows for 1.5 centimeters or less of needle 104, 112 to extend distally beyond distal end 134 of needle guard 106.

In some embodiments, as shown in FIGS. 6-7, needle guards 106 are transparent. The transparency allows a user to easily determine if and which needle is present within the guards to improve safety.

Figure 10:
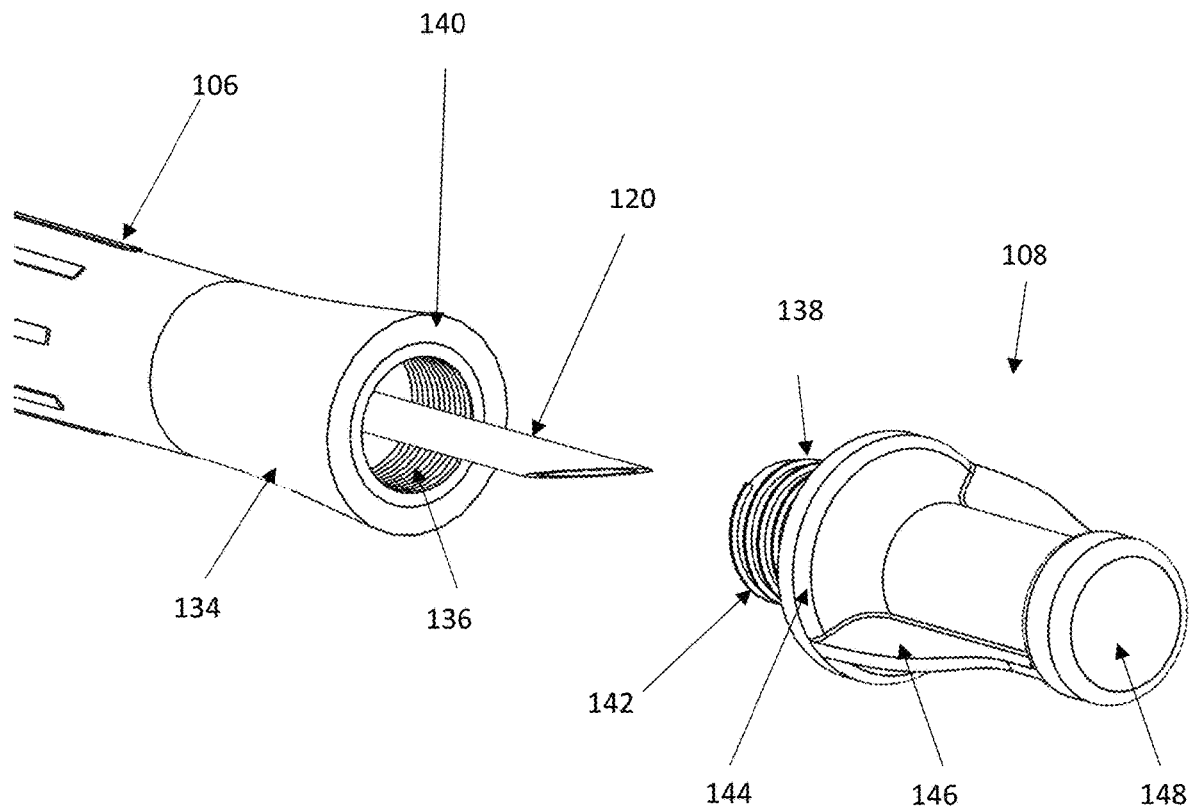
FIG. 10 is a close-up perspective view of the distal end of the aspiration needle and needle guard with the guard cap detached from the needle guard.

As best shown in FIG. 10, distal ends 134 of needle guards 106 include an attachment component to temporarily engage guard cap 108. As provided in the exemplary figures, the attachment component can be a helical thread 136 configured to engage a corresponding helical thread 138 on the proximal body portion of guard cap 108. The temporary attachment may be achieved through known approaches including but not limited to press fitting, cam locks, resilient clips, detents, etc.

Distal end 134 of needle guard 106 may further include a lateral expanse substantially greater than the outer diameter of needle 104, 112 to act as depth limiter 140 when puncturing the patient's tissue. In some embodiments, distal end 134 flares outwardly in a lateral direction as best shown in FIGS. 7-9 to further aid in stopping the depth of the needle penetration. Some embodiments alternatively or additionally include flanges at distal ends 134 of needle guards 106 to further aid in stopping the depth of the needle penetration.

In some embodiments, distal ends 134 of needle guards 106 are comprised of or include a layer of softer and more resilient material in comparison to the main body of needle guard 106. Distal end 134 thus provides some cushion when contacting the patient's tissue.

As previously noted, kit 102 may include guard caps 108. In some embodiments of kit 102, guard caps 108 are pre-attached to needle guards 106. In some embodiments of kit 102, needle guards 106 and guard caps 108 are pre-attached to needles 104, 112 as assemblies 107 and 109 depicted in FIGS. 2-3 and 7.

As best depicted in FIG. 6-7, guard caps 108 include an internal cavity configured to receive a distal portion of needle 104, 112. The length of the cavity corresponds to the length of the exposed needle tip when needle guard 106 is in place.

Referring back to FIG. 10, the proximal end of guard cap 108 includes proximal body 142 with helical thread 138 configured to engage thread 136 in distal end 134 of needle guard 106. While guard cap 108 includes proximal threaded body extension 142 and the distal end of needle guard 106 includes internal thread 136, this configuration can be reversed such that needle guard 106 includes a threaded body extension that is received by an internal thread in a proximal section of guard cap 108. In addition, guard cap 108 can be secured to needle guard 106 through alternative temporary attachments or attachment methods including but not limited to press fitting, cam locks, resilient clips, detents, etc.

Guard caps 108 further include a protective annular ring 144 that extends laterally beyond the outer diameter of proximal threaded body 142. Annular ring 144 is designed to provide a barrier between a clinician's fingertips and needle 104, 112 when the clinician is attaching guard cap 108 to needle 104, 112. If the clinician misses the opening to the cavity in guard cap 108, the sharpened tip of needle 104, 112 will contact protective annular ring 144 rather than penetrating the clinician's fingertips.

Guard caps 108 further include one or more laterally extending flanges 146 or other structural features to allow a user to rotate guard cap 108 more easily. Guard cap 108 further includes a closed, blunt distal end 148 to fully secure needle 104, 112 when not in use.

For embodiments in which the needle adapter 118 is configured to rotatably engage syringe 110, guard cap 108 and needle guard 106 may be configured to rotatably connect by rotating guard cap 108 in a direction that is opposite of the rotational direction to attach needle 104, 112 to syringe 110. For example, needle adapter 118 can be configured to rotatably engage syringe 110 by rotating needle 104, 112 in a clockwise direction and guard cap 108 can be removed by gripping flanges 146 on either side and rotating guard cap 108 in a clockwise direction. As a result, removing guard cap 108 does not accidentally remove needle 104, 112 from syringe 110.

In some embodiments, as exemplified in FIGS. 6-7, guard caps 108 are transparent. Transparency allows a user to easily determine if needles 104, 112 are present within needle guards 106 and guard caps 108 to improve safety.

Figure 11:
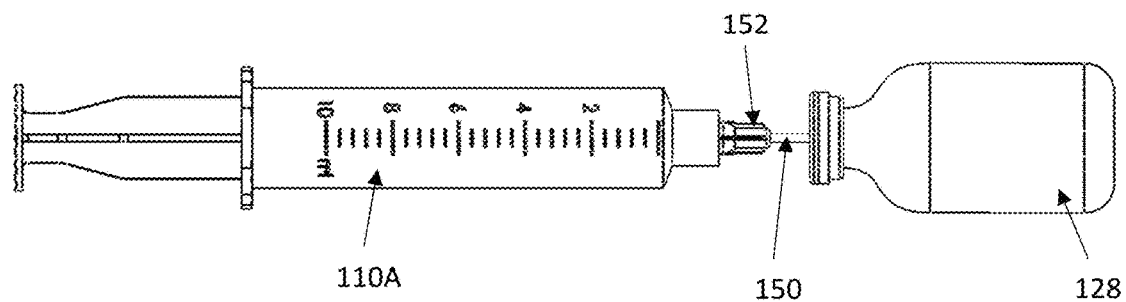
FIG. 11 is a side view of a syringe with an attached anesthetic retrieval needle inserted into a vial of anesthetic.
Figure 12:
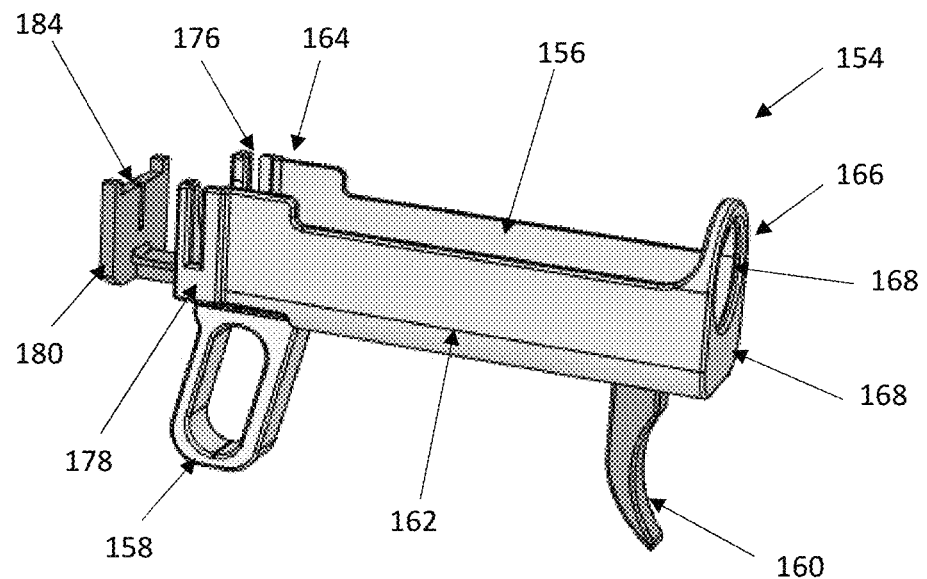
FIG. 12 is a perspective view of an embodiment of a single-handed syringe actuator.
Figure 13:
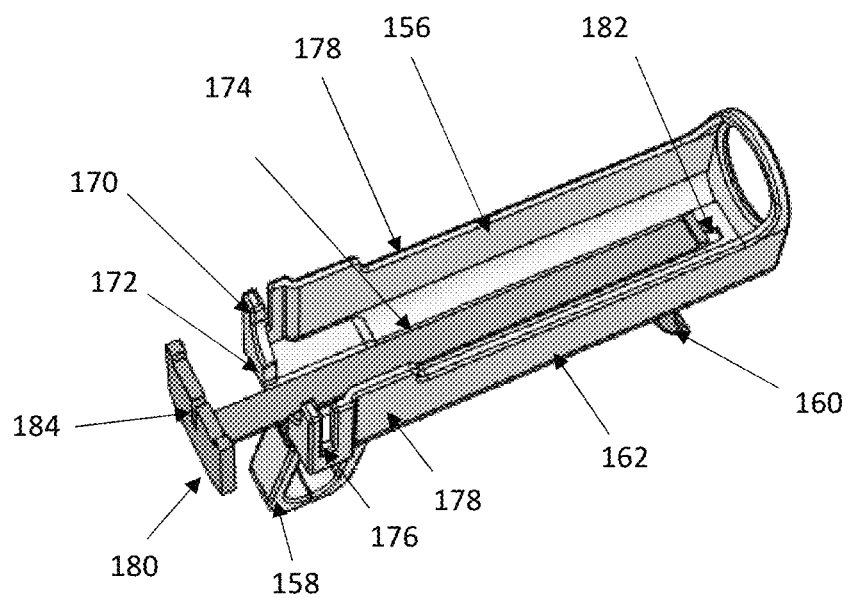
FIG. 13 is a top perspective view of the single-handed syringe actuator.

As shown in FIGS. 2-4, some embodiments of kit 102 include anesthetic retrieval needle 150. Anesthetic retrieval needle 150 is configured to attach to one of syringes 110 (e.g., anesthetic syringe 112) to retrieve fluidic anesthetic 113 from vial 128 or other fluid container as exemplified in FIG. 11. Thus, anesthetic retrieval needle 150 includes adapter 152 at a proximal end to engage syringe 110. Adaptor 152 can temporarily attach to syringe 110 in any of the ways described herein and/or can be the same form as adapters 118 from needles 104, 112.

In some embodiments, anesthetic retrieval needle 150 is an 18-gauge needle. However, some embodiments of anesthetic retrieval needle 150 have an alternatively sized inner diameter sufficient to retrieve anesthetic fluid from vial 128 or another container.

Anesthetic retrieval needle 150 can also have a blunt tip/distal end. While the tip of anesthetic retrieval needle 150 is sufficiently sharp to penetrate the barrier in vial 128, it can be relatively blunt in comparison to aspiration needles 104.

Anesthetic retrieval needle 150 is also smaller in length relative to aspiration needle 104. Anesthetic retrieval needle 150 simply needs to reach the fluid within vial 128, so the length can be generally the same or slightly longer than the depth of vial 128.

Kit 102 can also include vial 128 as exemplified in FIGS. 2-4. Vial 128 can be prefilled with an anesthetic. The anesthetic could be any anesthetic typically used in the peritonsillar abscess aspiration, such as lidocaine 1% with epinephrine.

Kit 102 can further include syringe actuator 154 as depicted in FIGS. 2-4 and 12-13. Syringe actuator 154 is preferably operable using a single hand to free up the clinician's other hand. As such, syringe actuator 154 includes syringe receiving area 156 and a pistol-like shape with handle 158 and trigger 160. Receiving area 156 is established by main body 162 having proximal end 164 and distal end 166 with receiving area 156 residing therebetween. Receiving area 156 is open at the top to receive syringe 110 and generally has a U-shaped cross-section so that syringe 110 snuggly fits therein.

Figure 14:
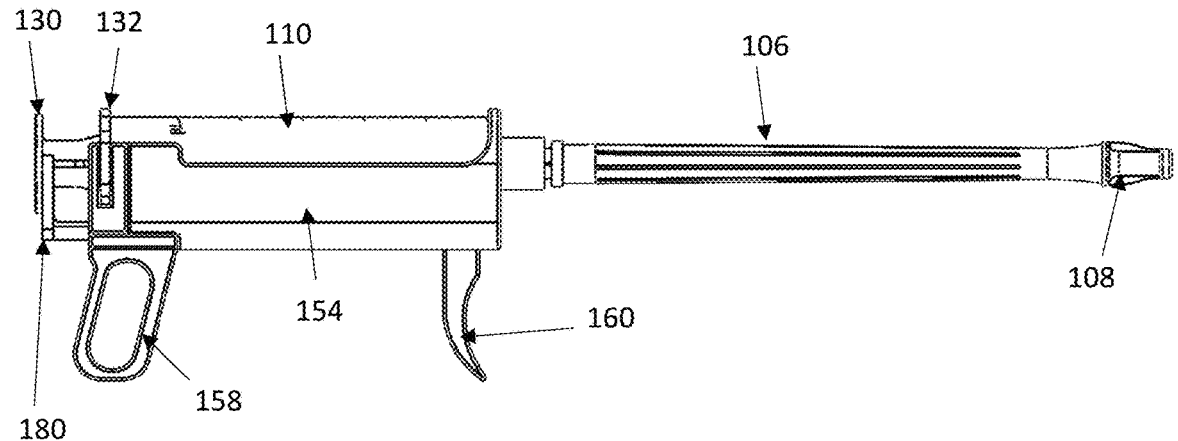
FIG. 14 is a side view of the assembly of the syringe, aspiration needle, needle guard, and guard cap with the syringe secured in the single-handed syringe actuator.

Proximal end 164 of main body 162 includes front wall 168 with aperture 170 to receive distal end 111 of syringe 110 and retain syringe 110 as depicted in FIGS. 14-16. Front wall 168 can have alternatively shaped apertures 170 so long as distal end 111 of syringe 110 can pass therethrough thereby allowing front wall 168 to aid in the retention of syringe 110 within main body 162 of syringe actuator 154.

Distal end 164 includes a pair of flange receipts 176 disposed in sidewalls 178 of main body 162. Flange receipts 176 are sized and shaped to receive barrel flanges 132 on syringe 110. In addition, flange receipts 176 are located at a point along the length of main body 162 such that barrel flanges 132 will be located at the same location when syringe 110 is secured within receiving area 156.

Distal end 164 of syringe actuator 154 further includes rear wall 170 with passage 172 disposed therein. Passage 172 allows actuator structure 174 to translate longitudinally through rear wall 170 relative to main body 162 when syringe actuator 154 is actuated.

Actuator structure 174 is in mechanical communication with trigger 160 at a first end and plunger contact 180 at the other end. Trigger 160 passes through channel 182 within the lower portion of main body 162 of syringe actuator 154, thereby allowing trigger 160 to translate with actuator structure 174. Channel 182 extends from a location proximate to proximal end 166 of main body 162 to handle 158 of main body 162.

Plunger contact 180 is designed to contact plunger flange 130 such that pulling trigger 160 causes a distally directed translation of plunger 126 relative to barrel 124 thereby creating a vacuum within barrel 124, which extends through an attached needle to extract material from the peritonsillar abscess. Plunger contact 180 can include one or more slots 184 configured to receive structural ribs 186 of plunger 126 thereby improving the connection between plunger 126 and plunger contact 180.

The effects of pulling trigger 160 are exemplified in comparing FIGS. 15 and 16. FIG. 15 depicts trigger 160 in an initial position in which the user has yet to attempt to extract material from the abscess. FIG. 16 depicts trigger 160 following a user pulling trigger 160 towards handle 158 to create the vacuum in syringe 110.

Figure 17:
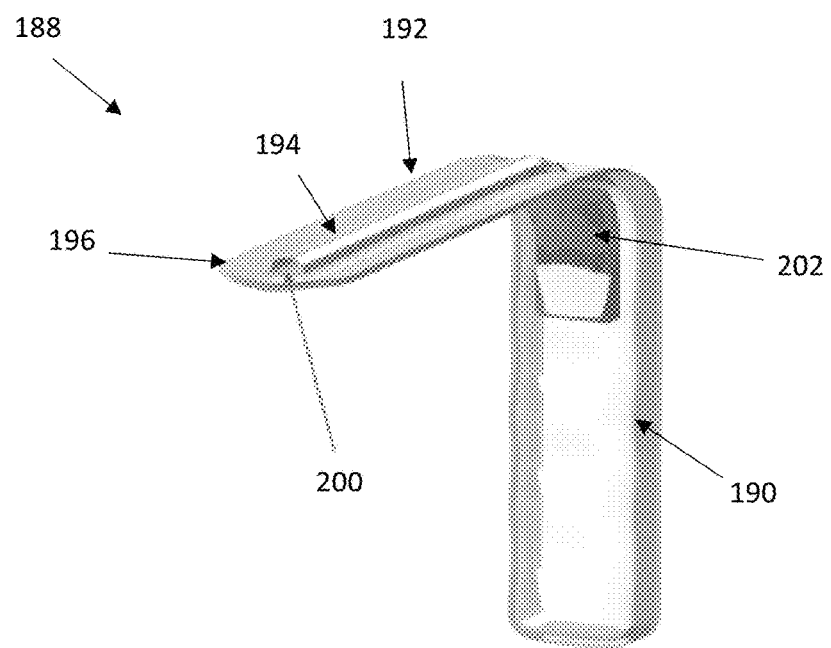
FIG. 17 is a front perspective view of an embodiment of the tongue depressor.
Figure 18:
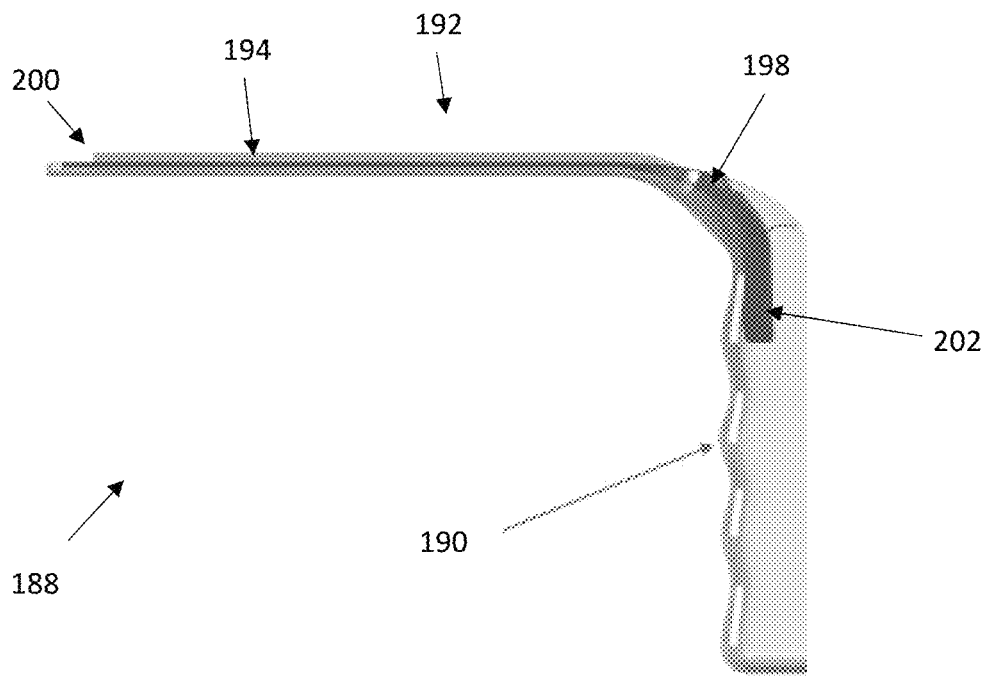
FIG. 18 is a side view of an embodiment of the tongue depressor.
Figure 19:
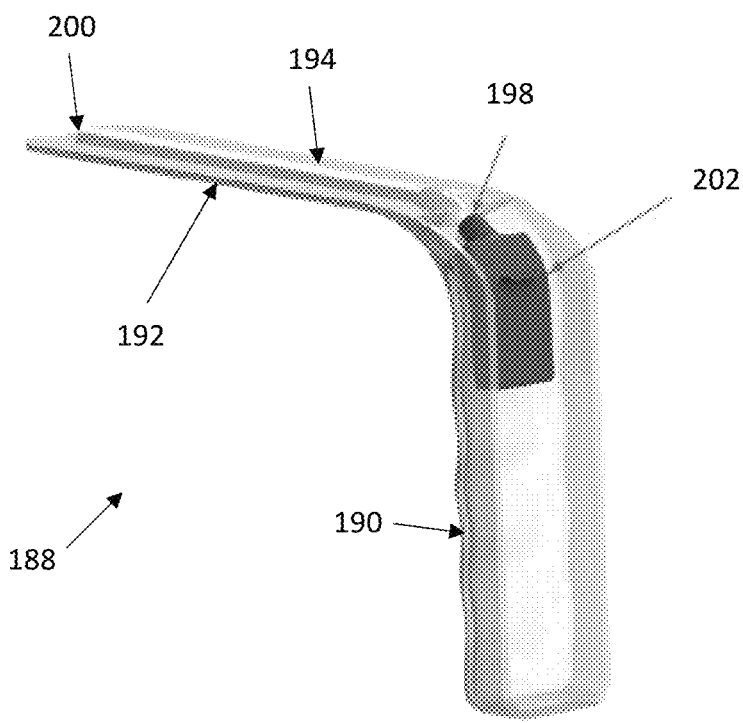
FIG. 19 is a rear perspective view of an embodiment of the tongue depressor.

Some embodiments of kit 102 further include tongue depressor blade 188 as shown in FIGS. 2-4. Tongue depressor blade 188, as depicted in FIGS. 17-19, includes an ergonomic handle 190 of about 10 centimeters with tongue depressor section 192 of about 15 centimeters. Tongue depressor blade 188 can include light guide 194 extending from handle section 190 to a location proximate distal end 196 of tongue depressor section 192. Light guide 194 is configured to guide light from light source 198 to distal end 200 of light guide 194, thereby projecting light into the patient's mouth during use.

Light source 198 can be located proximate handle section 190 and include a power source. The power source can be a battery in electrical communication with light source 198. The battery can reside within handle section 190 or within switch 202.

Light source 198 is controlled via switch 202. Switch 202 can be located near the upper end of handle section 190 where a user's thumb would be located during use. Switch includes a pull tab to allow for easy actuation. Sliding switch 202 up and towards tongue depressor section 192 completes the electrical circuit thereby providing power to light source 198, which provides light to light guide 194.

Figure 20:
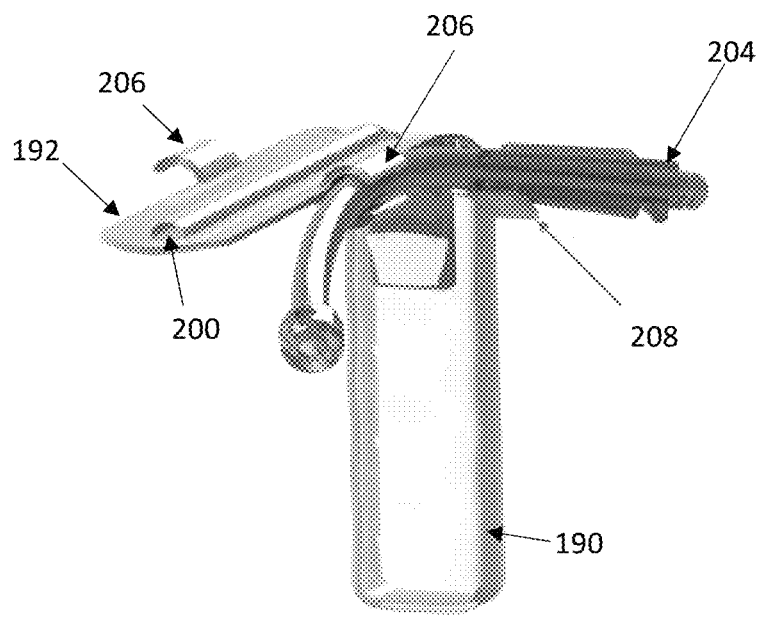
FIG. 20 is a front perspective view of an embodiment of the tongue depressor with the attached suction tube.
Figure 21:
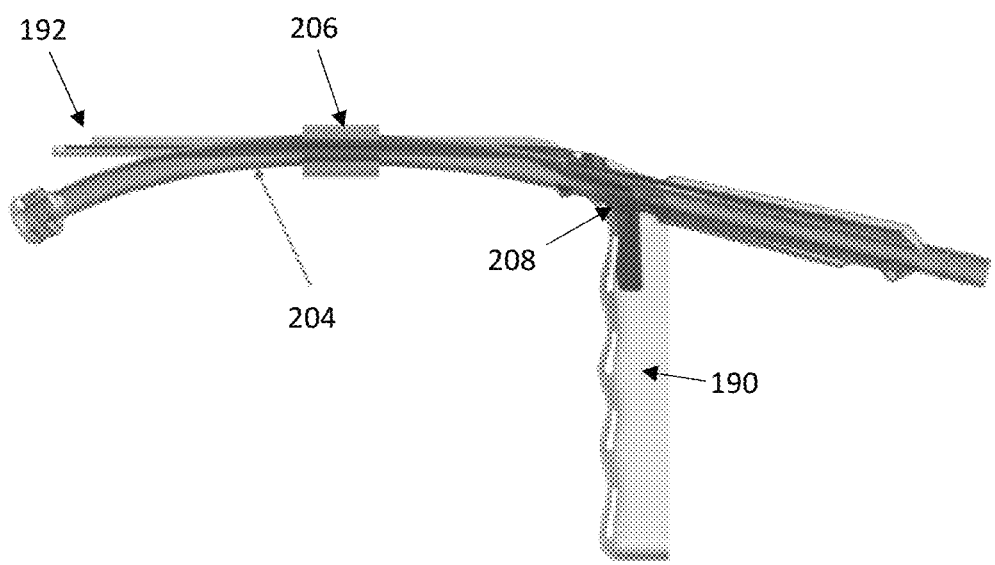
FIG. 21 is a side view of an embodiment of the tongue depressor with the attached suction tube.
Figure 22:
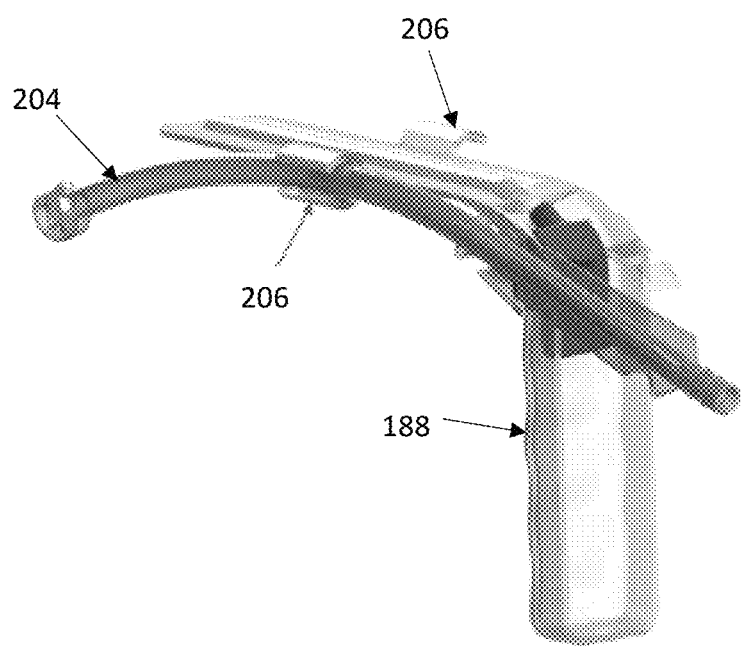
FIG. 22 is a rear perspective view of an embodiment of the tongue depressor with the attached suction tube.

As provided in FIGS. 2-4, kit 102 may include suction tube 204, such as the depicted Yankauer tube. In addition, as provided in FIGS. 20-22, tongue depressor 188 may include one or more tube clips 206 on one or both sides of tongue depressor 188. Tube clips 206 may be any clips configured to temporarily secure suction tube 204 to tongue depressor 188, including but not limited to resilient C-clips.

In addition, tongue depressor 188 may include shoulder flanges 208 on one or both sides of the tongue depressor. Shoulder flanges 208 are configured to help support and guide suction tube 204 when secured to tongue depressor 188.

The present invention further includes a method of using the components of kit 102 for aspirating a peritonsillar abscess. The method includes opening kit 102 and removing vial 128 of anesthetic fluid, anesthetic syringe 110A, and anesthetic retrieval needle 150. Anesthetic retrieval needle 150 is secured to anesthetic syringe 110A and then anesthetic retrieval needle 150 is inserted into vial 128. The plunger is retracted to withdraw anesthetic into barrel 124 of anesthetic syringe 110A.

Anesthetic retrieval needle 150 is detached from anesthetic syringe 110A and needle 150 be disposed. If kit 102 includes the anesthetic assembly 109 comprising of anesthetic application needle 112, needle guard 106, and guard cap 108, assembly 109 is removed from kit 102 and needle adaptor 118 is attached to anesthetic syringe 110A having the anesthetic therein. Tongue depressor 188 and suction tube 204 are also removed from kit 102. Guard cap 108 is removed from needle guard 106 and the clinician uses tongue depressor 188 to depress the patient's tongue while injecting the anesthetic.

Following completion of the anesthetic application, anesthetic syringe 110A and anesthetic application needle 112 can be disposed. The clinician can then remove syringe actuator 154 from kit 102 and attach the aspiration syringe 110B to syringe actuator 154. If aspiration needle assembly 107 is provided pre-assembled, then aspiration assembly 107, comprising aspiration needle 104 with the attached needle guard 106 and guard cap 108, is removed from kit 102. Using needle adapter 118, aspiration assembly 107 is attached to aspiration syringe 110B.

After the anesthetic has taken effect, the clinician can remove guard cap 108. Again, the clinician depresses the patient's tongue with tongue depressor 188 and then pierces the abscess with aspiration needle 104. The aspiration needle 104 is inserted until needle guard 106 abuts the abscess. The clinician then pulls trigger 160 to extract material from the abscess. If aspiration syringe 110A is filled and the abscess still needs to be further aspirated, guard cap 108 can be reattached to needle guard 106 and then aspiration needle 104 and guard assembly can be removed from aspiration syringe 110B. Aspiration syringe 110B can be emptied or a new aspiration syringe can be attached to syringe actuator 154. In addition, the previously used aspiration needle assembly 107 can be reused or it can be disposed and the remaining aspiration needle assembly 107 can be attached to aspiration syringe 110B to complete the procedure.

The clinician can optionally attach suction tube 204 to tongue depressor 188 and to a vacuum device at any point during the procedure. The clinician can then use suction tube 208 to help clear away excess fluids from the patient's mouth during the procedure.

Upon completion of the procedure, kit 102 and its contents can be disposed, or the contents can be sanitized using an autoclave or other sanitizing devices known in the art. For kits in which the contents are intended to be reused, the contents are comprised of a material that can withstand the sanitization process of an autoclave or other sanitizing devices.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A peritonsillar abscess aspiration kit, comprising:
    a hollow aspiration needle having a length extending between a distal tip and a proximal end that is greater than or equal to about 8.9 centimeters such that the distal tip can reach a peritonsillar abscess in a patient, wherein the distal tip is tapered to a point sufficient to puncture the peritonsillar abscess;
    an aspiration needle guard, the aspiration needle guard including:
        an internal lumen sufficiently sized to receive the aspiration needle therein;
        a length extending between a first end and a second end, wherein the length of the aspiration needle guard is less than the length of the aspiration needle, such that a distal section of the aspiration needle extends about 1 centimeter to about 1.5 centimeters beyond the second end of the aspiration needle guard when the aspiration needle resides within the internal lumen of the aspiration needle guard;
    an aspiration needle guard cap, the aspiration needle guard cap including:
        an open proximal end leading to an internal cavity, wherein the internal cavity is sufficiently sized to receive the distal section of the aspiration needle that extends beyond the second end of the aspiration needle guard when the aspiration needle resides within the internal lumen of the aspiration needle guard;
        a closed distal end;
    wherein the aspiration needle guard cap and aspiration needle guard are configured to temporarily attach to each other;
    at least one syringe configured to attach to the aspiration needle such that the distal tip of the aspiration needle is permanently fixed at a predetermined distance from a distal end of the syringe; and
    a syringe actuator configured to securely house the syringe, wherein the syringe actuator has a pistol grip and a trigger configured to proximally translate a plunger in the syringe when the trigger is pulled.

2. The kit of claim 1, further including a vial of anesthetic and an anesthetic retrieval needle for retrieving anesthetic from the vial.

3. The kit of claim 1, further including a suction tube.

4. The kit of claim 1, further including multiple syringes.

5. The kit of claim 1, further including a tongue depressor with a light source.

6. The kit of claim 1, wherein the aspiration needle guard is configured to attach to the needle hub and the aspiration needle guard has a length of at least 7.89 centimeters.

7. The kit of claim 1, wherein the proximal end of the aspiration needle guard cap is configured to attach to the second end of the aspiration needle guard.

8. The kit of claim 1, further including:
an anesthetic application needle having a length extending between a distal tip and a proximal needle hub;
an anesthetic needle guard, the anesthetic needle guard including:
an internal lumen sufficiently sized to receive the anesthetic application needle therein;
a length extending between a first end and a second end, wherein the length of the anesthetic needle guard is less than the length of the anesthetic application needle, such that a distal section of the anesthetic application needle extends beyond the second end of the anesthetic needle guard when the anesthetic application needle resides within the internal lumen of the anesthetic needle guard;
an anesthetic needle guard cap, the anesthetic needle guard cap including:
an open proximal end leading to an internal cavity, wherein the internal cavity is sufficiently sized to receive the distal section of the anesthetic application needle that extends beyond the second end of the anesthetic needle guard when the anesthetic application needle resides within the internal lumen of the anesthetic needle guard; and
a closed distal end.

9. A peritonsillar abscess aspiration kit, comprising:
a hollow aspiration needle having a length extending between a distal tip and a proximal end that is greater than or equal to about 8.9 centimeters such that the distal tip can reach a peritonsillar abscess in a patient, wherein the distal tip is tapered to a point sufficient to puncture the peritonsillar abscess and the proximal end is secured to a needle hub in a non-translatable manner;
an aspiration needle guard, the aspiration needle guard including:
an internal lumen sufficiently sized to receive the aspiration needle therein;
a length extending between a first end and a second end, wherein the length of the aspiration needle guard is less than the length of the aspiration needle, such that a distal section of the aspiration needle extends about 1 centimeter to about 1.5 centimeters beyond the second end of the aspiration needle guard when the aspiration needle resides within the internal lumen of the aspiration needle guard;
an aspiration needle guard cap, the aspiration needle guard cap including:
an open proximal end leading to an internal cavity, wherein the internal cavity is sufficiently sized to receive the distal section of the aspiration needle that extends beyond the second end of the aspiration needle guard when the aspiration needle resides within the internal lumen of the aspiration needle guard;
a closed distal end;
wherein the aspiration needle guard cap and aspiration needle guard are configured to temporarily attach to each other;
at least one syringe configured to attach to the aspiration needle such that the distal tip of the aspiration needle is permanently fixed at a predetermined distance from a distal end of the syringe.

10. The kit of claim 9, further including a vial of anesthetic and an anesthetic retrieval needle for retrieving anesthetic from the vial.

11. The kit of claim 9, wherein the length of the aspiration needle guard at least 7.89 centimeters.

12. The kit of claim 9, further including a suction tube.

13. The kit of claim 9, further including a tongue depressor with a light source.

14. The kit of claim 9, further including a syringe actuator configured to securely house the syringe, wherein the syringe actuator has a pistol grip and a trigger configured to proximally translate a plunger in the syringe when the trigger is pulled.

15. The kit of claim 9, wherein the proximal end of the aspiration needle guard cap is configured to attach to the second end of the aspiration needle guard.

16. The kit of claim 9, further including:
an anesthetic application needle having a length extending between a distal tip and a proximal needle hub;
an anesthetic needle guard, the anesthetic needle guard including:
an internal lumen sufficiently sized to receive the anesthetic application needle therein;
a length extending between a first end and a second end, wherein the length of the anesthetic needle guard is less than the length of the anesthetic application needle, such that a distal section of the anesthetic application needle extends beyond the second end of the anesthetic needle guard when the anesthetic application needle resides within the internal lumen of the anesthetic needle guard;
an anesthetic needle guard cap, the anesthetic needle guard cap including:
an open proximal end leading to an internal cavity, wherein the internal cavity is sufficiently sized to receive the distal section of the anesthetic application needle that extends beyond the second end of the anesthetic needle guard when the anesthetic application needle resides within the internal lumen of the anesthetic needle guard; and
a closed distal end.

17. A peritonsillar abscess aspiration needle assembly, comprising:
a hollow aspiration needle having a length extending between a distal tip and a proximal end, wherein the distal tip is tapered to a point sufficient to puncture an abscess, and the needle is configured to attach to a distal end of a syringe such that the distal tip of the aspiration needle is permanently fixed at a predetermined distance from a distal end of the syringe;
an aspiration needle guard, the aspiration needle guard including:
an internal lumen sufficiently sized to receive the aspiration needle therein;
a length extending between a first end and a second end, wherein the length of the aspiration needle guard is less than the length of the aspiration needle, such that a distal section of the aspiration needle extends beyond the second end of the aspiration needle guard when the aspiration needle resides within the internal lumen of the aspiration needle guard;

an aspiration needle guard cap, the aspiration needle guard cap including:
  an open proximal end leading to an internal cavity, wherein the internal cavity is sufficiently sized to receive the distal section of the aspiration needle that extends beyond the second end of the aspiration needle guard when the aspiration needle resides within the internal lumen of the aspiration needle guard;
  a closed distal end;
wherein the aspiration needle guard cap and aspiration needle guard are configured to temporarily attach to each other.

18. The assembly of claim 17, wherein the aspiration needle guard is transparent.

19. The assembly of claim 17, wherein the aspiration needle guard cap is transparent.

* * * * *